United States Patent [19]

Pachaly et al.

[11] Patent Number: 5,334,738
[45] Date of Patent: Aug. 2, 1994

[54] PROCESS FOR THE PREPARATION OF METHYLCHLOROSILANES

[75] Inventors: Bernd Pachaly; Volker Frey; Herbert Straussberger, all of Burghausen, Fed. Rep. of Germany

[73] Assignee: Wacker-Chemie GmbH, Munich, Fed. Rep. of Germany

[21] Appl. No.: 169,699

[22] Filed: Dec. 20, 1993

[30] Foreign Application Priority Data

Feb. 9, 1993 [DE] Fed. Rep. of Germany ....... 4303766

[51] Int. Cl.$^5$ .............................................. C07F 7/16
[52] U.S. Cl. .................................................... 556/472
[58] Field of Search ......................................... 556/472

[56] References Cited

U.S. PATENT DOCUMENTS

| | | | |
|---|---|---|---|
| 3,536,743 | 10/1970 | Schrader et al. | 556/472 |
| 3,560,545 | 2/1971 | Schrader et al. | 556/472 |
| 4,281,149 | 7/1981 | Shade | 556/472 |
| 4,450,282 | 5/1984 | Ritzer et al. | 556/472 |
| 5,015,751 | 5/1991 | Feldner et al. | 556/472 |
| 5,250,716 | 10/1993 | Mui | 556/472 |
| 5,281,739 | 1/1994 | Halm et al. | 556/472 |

OTHER PUBLICATIONS

M. P. Clarke, Journal of Organometallic Chemistry, 376 (1989) pp. 165–222.
W. J. Ward et al. Journal of Catalysis, 100 (1986) pp. 240–249.
F. Dubrous et al., Electric Furnace Conf. Proc. 1990, pp. 241–247.
A. Schei et al., Proc. Conf. Silicon for Chemical Industry, 1992, pp 11–23.
G. Schüssler et al., Proc. Conf. Silicon Metal for Chemical Industry, 1992, pp. 39–46.
H. Rong et al., Proc. Conf. Silicon Metal for Chemical Industry, 1992 pp. 67–83.

Primary Examiner—Paul F. Shaver
Attorney, Agent, or Firm—Martin Connaughton

[57] ABSTRACT

Methylchlorosilanes are prepared from silicon and methyl chloride in the presence of a copper catalyst and optionally promoter substances, the production rates of the individual methylchlorosilanes, based on the surface area of the silicon employed, being controlled by the structural parameter QF of the silicon. The structural parameter QF is determined by (a) cutting up silicon test specimens to form a cut surface,
(b) totaling on the cut surface the areas of the precipitates of intermetallic phases having a longitudinal shape to give an area number A,
(c) totaling on the cut surface the areas of precipitates of intermetallic phases having a circular shape to give an area number B, and
(d) obtaining the quotient of the area number A and the area number B, called the structural parameter QF.

4 Claims, 4 Drawing Sheets

PROCESS FOR THE PREPARATION OF METHYLCHLOROSILANES

FIELD OF THE INVENTION

The present invention relates to a process for the preparation of methylchlorosilanes by direct synthesis using silicon having certain structural features.

BACKGROUND OF INVENTION

In the direct synthesis of methylchlorosilanes from silicon and methyl chloride by the Rochow process in the presence of a copper catalyst and optionally, promoter substances, a mixture of the methylchlorosilanes, and a smaller amount of other by-products, are formed. The mechanism and the product spectrum are described, for example, in M. P. Clarke, Journal of Organometallic Chemistry, 376 (1989) 165–222. The influence of the catalyst and the promoters is described, for example, in W. J. Ward et al., Journal of Catalysis, 100 (1986) pages 240–249.

Silicon metal is produced in electrically heated furnaces by reduction of silicon dioxide with carbon, optionally with admixed wood chips. The crude product is brought to the purity required for the preparation of methylchlorosilanes by suitable refining processes. The refined silicon is then usually cast from the refining crucibles into iron troughs, from which it is removed after solidification and prepared by breaking and sieving. It is ground to particle sizes of about 500 µm for use in the direct synthesis.

The requirements on the silicon in respect of chemical composition and particle size distribution for the direct synthesis have been investigated relatively thoroughly. The structural composition and its influence on the reaction with methyl chloride has been the subject of scientific studies only recently. EP-A 350 683 discloses that the structure, which is determined by the cooling process during production of the silicon metal, has an influence on the direct synthesis, because silicon metal produced by atomization gives increased production rates.

The structure of the silicon metal is determined by the size of the crystals of the polycrystalline silicon and the composition and position of the intermetallic phases which precipitate out from the main impurities, for example Al, Ca, Fe and Ti, with silicon in the course of cooling and solidification during the preparation process. The composition of these phases is described, inter alia, in F. Dubrous et al., Electric Furnace Conf. Proc., 1990, pages 241–247, and the ability to influence the formation of these phases is described by A. Schei et al., Proc. Conf. Silicon for Chemical Industry, 1992, pages 11–23. A process for improving the properties by rapid solidification is described by G. Schüssler et al., Proc. Conf. Silicon Metal for Chemical Industry, 1992, pages 39–46, and the influence of the crystal structure on the direct synthesis is described by H. Rong et al., Proc. Conf. Silicon Metal for Chemical Industry, 1992, pages 67–83.

It is thus known that the yield and selectivity of the direct synthesis depends on the structure of the silicon, it being possible for the structure to be influenced by choosing the cooling conditions during the solidification process of the silicon and optionally subsequent annealing.

SUMMARY OF INVENTION

The object of the present invention was to provide an improved process for the direct synthesis of methylchlorosilanes in which the desired methylchlorosilanes can be prepared at the highest possible production rates and the amount of by-products obtained is as low as possible. Another object of the invention was to describe silicon with which the best production rate for the desired methylchlorosilanes, particularly dimethyldichlorosilane, can be achieved by structural parameters, so that silicon having the desired structure can be prepared.

The invention relates to a process for the preparation of methylchlorosilanes from silicon and methyl chloride in the presence of a copper catalyst and optionally, promoter substances, in which the production rates of the individual methylchlorosilanes, based on the surface area of the silicon employed, are controlled by the structure of the silicon, the process comprising selecting the silicon having the desired structure on the basis of its structural parameter QF. The structural parameter QF being determined by (a) cutting up silicon test specimens to form a cut surface,
(b) totaling on the cut surface the areas of precipitates of intermetallic phases having a longitudinal shape to give an area number A,
(c) totaling on the cut surface the areas of precipitates of intermetallic phases having a circular shape to give an area number B, and
(d) obtaining the quotient of the area number A and the area number B, called the structural parameter QF.

In the process according to the invention, the structural features of the silicon are described by the structural parameter QF, which is accessible by a novel method of structure analysis. The correlation of the structural parameters QF of various types of silicon structure with the behavior thereof during the direct synthesis allows optimum structural features to be recognized in the silicon and thus allows the selectivity and yields to be controlled in the desired direction for the desired methylchlorosilanes.

During cooling and solidification, pure, primary silicon separates out in the form of crystallites which are separated by grain boundaries. In addition to the primary silicon, precipitates of intermetallic phases, as well as pores and inclusion of slag, form in the silicon. The precipitates of intermetallic phases occur preferably in the circular shape within the crystallites and more preferably in the longitudinal shape along the grain boundaries.

Primary silicon, intermetallic phases, pores and slag can be distinguished, for example, in a black-and-white image via the gray level, and intermetallic phases in the primary silicon and along grain boundaries can be distinguished, for example, via the degree of roundness.

A preferred embodiment for determination of the structural parameter QF of silicon metal comprises casting silicon test specimens with a diameter of about 5 to 25 mm in a casting resin, as is customary in metallography. After grinding and polishing, images are reflected via an optical microscope in 10- to 1000-fold magnification via a video camera into a commercially available image analyzing system, for example Quantimet® 500 from Leitz. The result produced by the image analysis, which is carried out in the manner described in the operating manual, is the area content of the longitudinal intermetallic phases as the area number A and the area content of the circular intermetallic phases as the area number B. The image analyzing system differentiates, for example, between the longitudinal shapes and the circular shapes with the aid of the particular degree of roundness. For example, shapes having a degree of roundness of >2 are classified as longitudinal, and shapes having a degree of roundness of $\leq 2$ are classified as circular. A value of 1.5 to 2.5 is preferably chosen as the degree of roundness for classification as longitudinal or circular.

FIG. 1 shows the cut surface of a ground and polished silicon test specimen in approximately 250-fold magnification under an optical microscope. The longitudinal (1) and the circular (2) precipitates of intermetallic phases are emphasized graphically.

In some grades of silicon, especially if these have been prepared by rapid cooling, the precipitates of intermetallic phases, which occur preferentially along the grain boundaries, can sometimes appear as chain-like rows of circular shapes. These chain-like precipitates of intermetallic phases are then to be added to the area content A. This can be effected, for example, by joining the intermetallic phases in question by very thin lines, which are inserted into the image by a computer operation, and converting the chain-like precipitates into longitudinal particles.

For silicon metal having the elemental composition usually employed in the direct synthesis of methylchlorosilanes (Al 0.10–0.28% by weight, Ca 0–0.15% by weight, Fe 0.15–0.50% by weight, Ti 0.015–0.05% by weight), the quotient QF=A/B is determined by the solidification conditions and can thus be used as the structural parameter QF for describing the structural features.

The precipitates of intermetallic phases in a circular shape can be distinguished from the precipitates of intermetallic phases in a longitudinal shape and the area numbers A and B can be determined and the structural parameter QF calculated by any other desired method, for example, using an electron microscope.

The production rate, based on the surface area of the silicon $$PR = \frac{\text{weight of methylchlorosilane}}{\text{surface area of silicon} \times \text{unit time}} \quad \frac{\text{mg}}{\text{m}^2 \times \text{min}}$$

is quoted as the decisive parameter for indicating the space/time yield for a particular methylchlorosilane using a particular type of silicon. The rate is related to the surface area because the reactions take place on the surface of the silicon. Furthermore, in modern direct synthesis processes, not all the silicon fed in is consumed without trace, but silicon is diverted out before the ratio of silicon, catalyst and promoters proves to be unfavorable. A particular advantage is that the production rate thus determined is independent of the surface area of the silicon.

It should be possible to prepare a certain methylchlorosilane at the highest possible production rate, and the amount of undesirable by-products obtained should be as low as possible. To determine this requirement numerically, the production rates of the by-products are subtracted from the production rate (PR) of the target product. For example, a direct synthesis process in which dimethyldichlorosilane (M2) is prepared, in addition to the smallest possible amounts of methyltrichlorosilane (M1), high-boiling components (HB) of boiling range 75° C. to 165° C. at 0.1 mPa and methyldichlorosilane (HM), is particularly desirable because M1, HB and HM do not have the same economic value, since their given usefulness is limited in terms of quantity.

Expressed as an equation, the desired direct synthesis process should then have the highest possible production rate PRM2−(PRM1+PRHB+PRHM), in which PRM2 is the production rate of M2. This high production rate is achieved if silicon having the structural parameter QF of 18 to 60, in particular 25 to 35, is employed in the process according to the invention, the areas of the precipitates of intermetallic phases having a longitudinal shape with a degree of roundness of >2 being totaled to give the area number A and the areas of the precipitates of intermetallic phases having a circular shape with a degree of roundness of $\leq 2$ being totaled to give the area number B for determination of the structural parameter.

The degree of roundness is calculated from the known formula $$\text{degree of roundness} = \frac{\text{circumference}}{4 \times \pi \times \text{area} \times 1.064}.$$

The reactivity and selectivity of silicon metal is a function of the structure in the synthesis of methylchlorosilanes at a constant chemical composition and under constant reaction conditions, such as pressure, temperature, amount of methyl chloride, amount of catalyst and particle size of the silicon. The structure is determined by the cooling rate during the solidification process.

Slow cooling of the liquid silicon leads to small structural parameters QF and rapid cooling leads to high values. Numerous processes which are known per se for cooling are suitable for adjusting the desired structural parameter. For example, in the most frequent procedure for the solidification process, the liquid silicon is introduced into a cast iron casting trough, in which it solidifies. Structural parameters QF, which can be determined by the above preferred embodiment, of 0.05 to 0.25 can be achieved, for example, by insulating the casting trough from the outside with silicon dust and casting the silicon onto a layer of silicon dust in the casting trough.

Structural parameters QF of up to about 7 are achieved by lower casting heights and thinner insulation. Values of up to about 11 are obtained by cooling the casting trough, by casting thin coats in a plurality of layers or by continuous casting on silicon granules. Structural parameters QF of 18 to 60 can be achieved by casting silicon in water, it being possible for the structural parameter QF to be adjusted precisely in the range of from 25 to 35 by, varying the granule size of the water-granulated silicon. The silicon obtained by, for example, the process of G. Schüssler et al., Proc. Conf. Silicon Metal for Chemical Industry, 1992, page 39–46 by atomization in air has structural parameters QF of more than 60.

The silicon grades usually employed for the direct synthesis have structural parameter QF of about 2 to 5. In the range of very slow cooling, with a silicon having the structural parameter QF of 0.1 to 2, temperature effects with diffusion and formation of new intermetallic phases overlap the solidification process. The production rate of crude silane thereby rises. The production rate of crude silane also rises with rapid cooling. Atomized silicon leads to the highest known production rates of crude silane. However, the highest production rate of PRM2−(PRM1+PRHB+PRHM) is reached only by using the process according to the invention, because silicon having the optimum structural parameters is thereby employed in a specific manner.

In the following example, unless stated otherwise in each case,
(a) all the quantitative data relate to the weight;
(b) all the pressures are 0.10 mPa (absolute);
(c) all the temperatures are 20° C., and
(d) the abbreviation "QF" means—the structural parameter QF

EXAMPLE (a) Silicon types

A series of 13 types of silicon of similar chemical composition which represent the industrial possibilities for controlling solidification conditions were investigated for their structural parameter QF and, in a standardized laboratory test for reaction with methyl chloride by the direct synthesis process, for their efficiency.

The contents of the aluminum calcium and iron impurities in percent by weight, the structural parameters QF determined by the above preferred embodiment and the particular solidification conditions chosen for the silicon structure types are shown in Table 1.

For silicon types No. 1-9, the liquid silicon was introduced into a cast iron casting trough, in which it solidified. The casting trough was insulated from the outside with silicon dust in some cases. In some cases, the silicon was cast onto a layer of silicon dust on the base and on the walls of the casting trough. The thin layer of silicon dust was about 2–5 mm and the thick layer of silicon dust was about 10–20 mm. For silicon types No. 11 and 12, the liquid silicon was cast in water. For silicon type No. 13, liquid silicon was atomized in air by the process of G. Schüssler et al., Proc. Conf. Silicon Metal for Chemical Industry, 1992, pages 39–46.

TABLE 1

| Si type | Al | Ca | Fe | Structural parameter QR | Solidification process |
|---|---|---|---|---|---|
| No. 1 | 0.19 | 0.010 | 0.28 | 0.10 | Trough insulated/casting onto thick Si dust layer, casting height 35 cm |
| No. 2 | 0.18 | 0.014 | 0.18 | 0.25 | Trough insulated/casting on thin Si dust layer, casting height 50 cm |
| No. 3 | 0.18 | 0.019 | 0.28 | 0.26 | Trough not insulated/casting on thick Si dust layer, casting height 40 cm |
| No. 4 | 0.18 | 0.011 | 0.21 | 1.58 | Trough not insulated/casting on thin Si dust layer, casting height 40 cm |
| No. 5 | 0.26 | 0.047 | 0.41 | 2.34 | Trough not insulated/casting on thin Si dust layer, casting height 30 cm |
| No. 6 | 0.17 | 0.025 | 0.37 | 3.19 | Trough not insulated, 4 layers of 15 cm, 2nd layer from top |
| No. 7 | 0.21 | 0.016 | 0.54 | 4.13 | Trough not insulated/casting on thin Si dust layer, casting height 15 cm |
| No. 8 | 0.17 | 0.038 | 0.47 | 6.02 | Trough not insulated/casting on thin Si dust layer, casting height 10 cm |
| No. 9 | 0.26 | 0.061 | 0.34 | 7.86 | Trough not insulated/casting in trough without Si dust layer, casting height 8 cm, trough water-cooled |
| No. 10 | 0.21 | 0.022 | 0.39 | 10.09 | Continuously cast on Si granules, casting height 1 cm |
| No. 11 | 0.24 | 0.056 | 0.39 | 23.21 | Water-granulated, 10–15 mm diameter |
| No. 12 | 0.19 | 0.027 | 0.25 | 29.55 | Water-granulated, 5–10 mm diameter |
| No. 13 | 0.28 | 0.004 | 0.28 | 63.92 | Atomized, diameter 50–500 μm |

(b) Direct reaction

The above silicon types 1 to 13 were employed in a standardized test process for the direct reaction of silicon with methyl chloride in the presence of a copper catalyst to give methylchlorosilanes:

120 g of silicon powder of known specific surface area and of particle size 70–250 μm, mixed with a catalyst mixture of 6 g of copper(II) oxide, 1 g of zinc oxide and 6 mg of tin powder, were initially introduced into a laboratory fluidized-bed reactor with a heating coil, gas distribution frit, distillation bridge with brine cooling and graduated receiver vessel. After heating to 350° C., 40 liter/hour of methyl chloride were added. Formation of the crude silane started after 24 to 37 minutes. The first 50 ml of crude silane were collected and discarded. 30 ml of crude silane were then collected and the time for production of this amount was recorded. The crude silane composition was determined in percent by weight by means of gas chromatography.

Table II shows the time taken for the reaction to start=T in minutes, the production rate of crude silane=PRC $$PRC = \frac{\text{weight of crude silane}}{\text{surface area of the silicon} \times \text{unit time}} \quad \frac{mg}{m^2 \times min}$$

at an Si conversion interval of 9–14% and the composition of the crude silane with respect to the most important components of methyldichlorosilane=HM, methyltrichlorosilane=M1, trimethylchlorosilane=M3, dimethyldichlorosilane=M2 and high-boiling components=HB in percent by weight. Components in the boiling range from 75°–165° C. are described as high-boiling components.

TABLE II

| Silicon types | QF | T | HM | M1 | M3 | M2 | HB | PRC |
|---|---|---|---|---|---|---|---|---|
| No. 1 | 0.10 | 37 | 0.82 | 6.40 | 3.52 | 82.57 | 6.40 | 87 |
| No. 2 | 0.25 | 31 | 0.82 | 6.72 | 3.31 | 84.40 | 4.51 | 78 |
| No. 3 | 0.26 | 32 | 0.67 | 7.57 | 3.77 | 83.77 | 4.04 | 87 |
| No. 4 | 1.58 | 30 | 0.71 | 8.51 | 4.06 | 82.39 | 4.05 | 75 |
| No. 5 | 2.34 | 29 | 1.07 | 7.79 | 4.03 | 83.11 | 4.21 | 61 |
| No. 6 | 3.19 | 26 | 1.03 | 7.54 | 3.63 | 83.50 | 3.97 | 79 |
| No. 7 | 4.13 | 25 | 0.78 | 7.30 | 3.78 | 84.24 | 3.98 | 89 |
| No. 8 | 6.02 | 26 | 0.56 | 6.90 | 3.64 | 84.88 | 3.82 | 97 |
| No. 9 | 7.86 | 26 | 0.94 | 6.79 | 3.62 | 85.19 | 3.26 | 99 |
| No. 10 | 10.09 | 24 | 0.96 | 6.92 | 3.50 | 85.32 | 3.02 | 105 |
| No. 11 | 23.21 | 30 | 1.97 | 5.97 | 2.53 | 86.11 | 3.02 | 118 |
| No. 12 | 29.55 | 31 | 2.25 | 5.75 | 2.58 | 86.07 | 2.80 | 120 |

TABLE II-continued

| Silicon types | QF | T | HM | M1 | M3 | M2 | HB | PRC |
|---|---|---|---|---|---|---|---|---|
| No. 13 | 63.92 | 33 | 3.78 | 7.77 | 2.14 | 81.20 | 2.59 | 125 |

The results from Table II are plotted as a graph in FIG. 2. The structural parameters QF of the silicon types employed are plotted on the abscissa. The production rate of crude silane PRC in mg/m² x minutes on the one hand and the start-up time T in minutes on the other hand are plotted on the left ordinate. The content of the various silanes in percent by weight is plotted on the right ordinate, except the content of M2, which is also plotted on the left.

The production rates for the main components PRM2, PRM1, PRM3, PRHB and PRHM in mg/m² x minute were determined from the production rate for the crude silane PRC and the weight contents of the main components M2, M1, HB, M3 and HM, and are shown in Table III.

TABLE III

| Silicon types | PRHM | PRM2 | PRM1 | PRHB | PRM3 |
|---|---|---|---|---|---|
| No. 1 | 0.71 | 71.84 | 5.57 | 5.57 | 3.06 |
| No. 2 | 0.64 | 65.83 | 5.24 | 3.52 | 2.58 |
| No. 3 | 0.58 | 72.88 | 6.59 | 3.51 | 3.28 |
| No. 4 | 0.53 | 61.79 | 6.38 | 3.04 | 3.05 |
| No. 5 | 0.65 | 50.70 | 4.75 | 2.57 | 2.46 |
| No. 6 | 0.81 | 65.97 | 5.96 | 3.14 | 2.87 |
| No. 7 | 0.69 | 74.97 | 6.50 | 3.54 | 3.36 |
| No. 8 | 0.54 | 82.33 | 6.69 | 3.71 | 3.53 |
| No. 9 | 0.94 | 84.34 | 6.72 | 3.23 | 3.58 |
| No. 10 | 1.01 | 89.59 | 7.27 | 3.17 | 3.68 |
| No. 11 | 2.32 | 101.61 | 7.04 | 3.56 | 2.99 |
| No. 12 | 2.7 | 103.28 | 6.90 | 3.36 | 3.10 |
| No. 13 | 4.73 | 101.5 | 9.71 | 3.24 | 2.68 |

The results from Table III are plotted as a graph in FIG. 3. The structural parameters QF of the silicon types employed are plotted on the abscissa. The production rate of crude silane in mg/m² x minute for the various silanes is plotted on the ordinate.

The silicon which is most suitable for the preparation of M2 has a high production rate of PRM2−(PRM1+PRHB+PRHM). Silicon having the structural parameter QF of 18 to 60, in particular 25 to 35, proves to be the optimum here. The water-granulated silicon types No. 11 and 12 are in the optimum range.

In FIG. 4, the structural parameters QF of the silicon types employed are plotted on the abscissa. The production rate PRM2−(PRM1+PRHB+PRHM) in mg/m² x minute is plotted on the ordinate.

Figure 1:
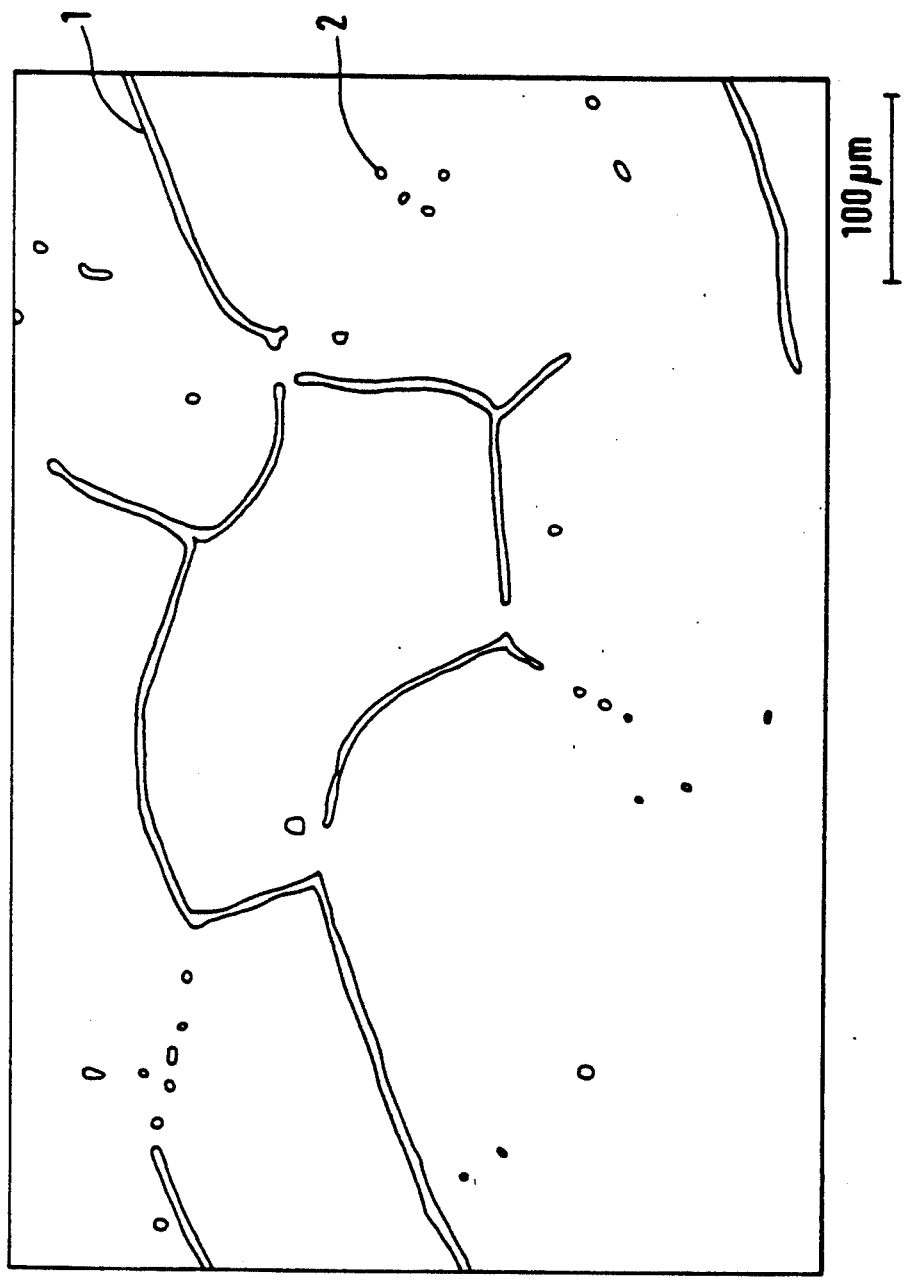
FIG. 1 shows the cut surface of a ground and polished silicon test specimen in approximately 250-fold magnification.
Figure 2:
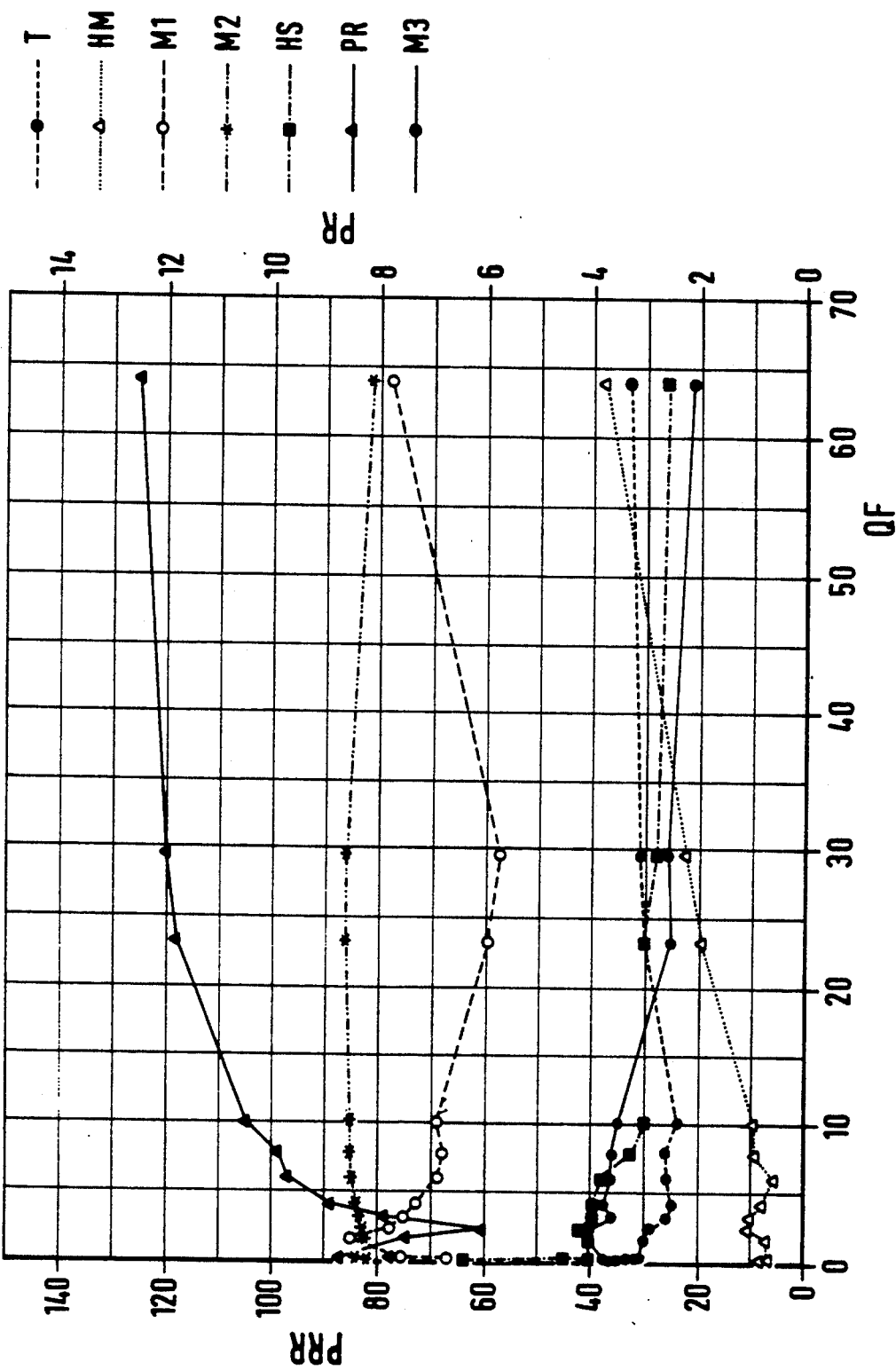
FIG. 2 shows the results from Table II plotted as a graph.
Figure 3:
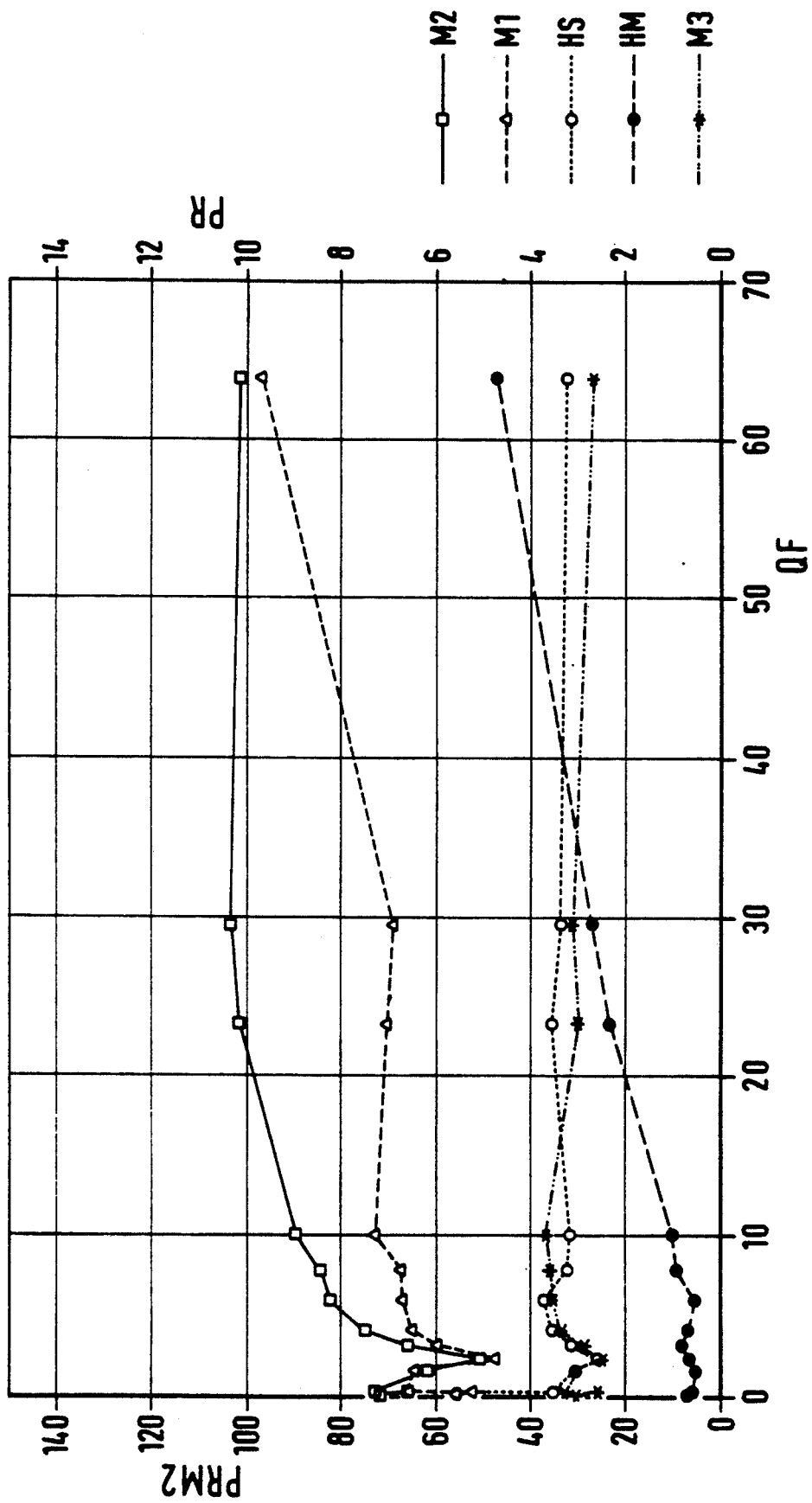
FIG. 3 shows the results of Table III plotted as a graph.
Figure 4:
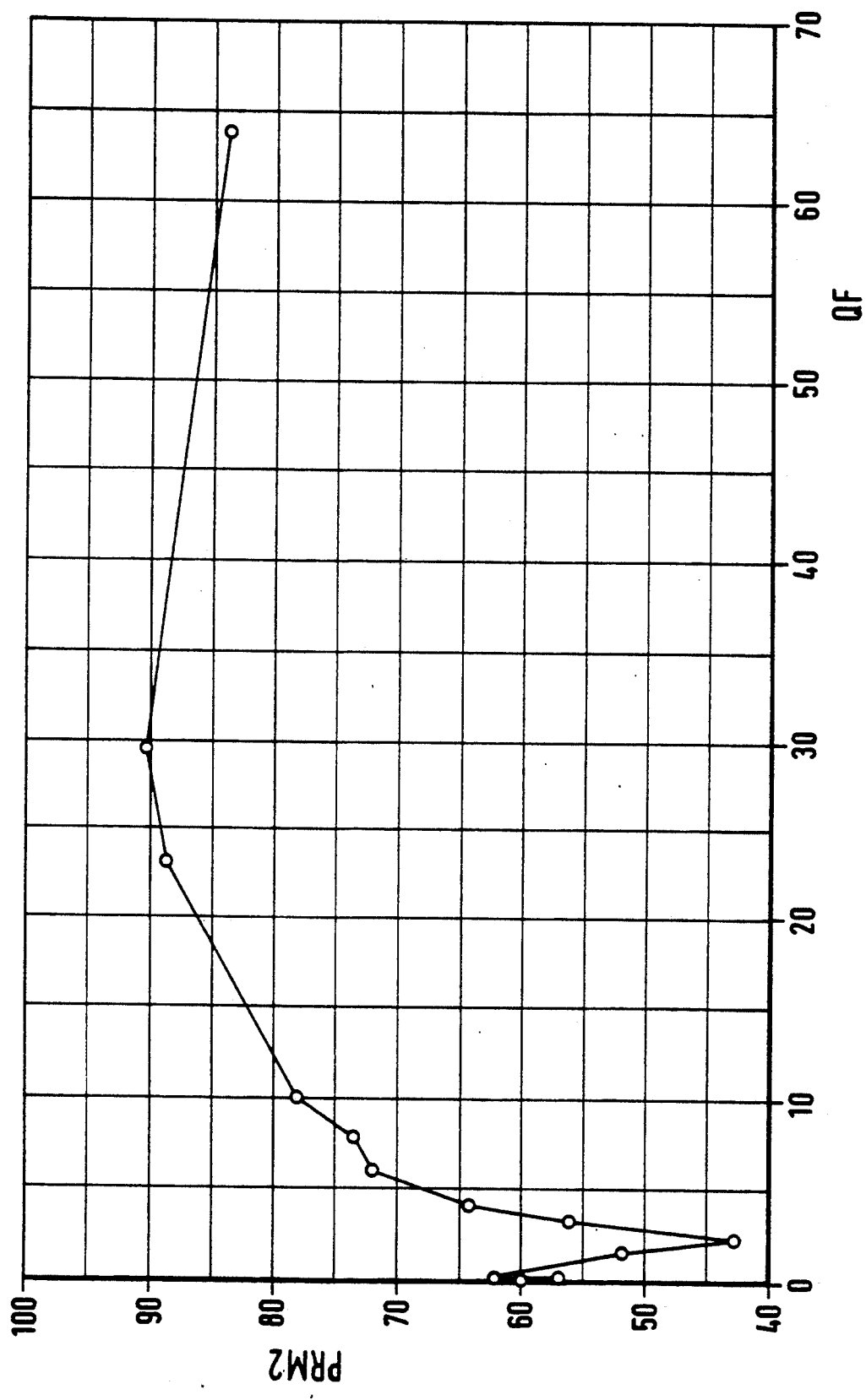
FIG. 4 shows the structural parameters of the Si types employed plotted on the abscissa with the production rate plotted on the ordinate.

What is claimed is:

1. A process for the preparation of methylchlorosilanes from silicon and methyl chloride in the presence of a copper catalyst and wherein promoter substances may be employed, in which the production rates of the individual methylchlorosilanes, based on the surface area of the silicon employed, are controlled by the structure of the silicon, which comprises selecting the silicon having the desired structure on the basis of its structural parameter QF, the structural parameter QF being determined by
   (a) cutting up silicon test specimens to form a cut surface,
   (b) totaling on the cut surface the areas of precipitates of intermetallic phases having a longitudinal shape to give an area number A,
   (c) totaling on the cut surface the areas of precipitates of intermetallic phases having a circular shape to give an area number B, and
   (d) obtaining the quotient of the area number A and the area number B, called the structural parameter QF.

2. The process as claimed in claim 1, wherein silicon having the structural parameter QF of 18 to 60 is employed, the areas of the precipitates of intermetallic phases having a longitudinal shape with a degree of roundness of >2 being totaled to give the area number A and the areas of the precipitates of intermetallic phases having a circular shape with a degree of roundness of ≦2 being totaled to give the area number B for determination of the structural parameter.

3. The process as claimed in claim 1, wherein water-granulated silicon is employed.

4. The process as claimed in claim 2, wherein water-granulated silicon is employed.

* * * * *